United States Patent [19]

Spear et al.

[11] Patent Number: 5,330,904
[45] Date of Patent: Jul. 19, 1994

[54] METHOD FOR MAMMALIAN CELL TRANSFECTION USING 25-HYDROXYCHOLESTEROL

[75] Inventors: David H. Spear, Playa del Rey; Peter A. Edwards, Los Angeles, both of Calif.

[73] Assignee: Regents of the University of California, Oakland, Calif.

[21] Appl. No.: 899,745

[22] Filed: Jun. 17, 1992

[51] Int. Cl.$^5$ .................. C12N 15/00; C12N 1/00; C12N 1/14; C12Q 1/68
[52] U.S. Cl. .................. 435/172.3; 435/6; 435/7.21; 435/948; 935/52; 935/55
[58] Field of Search .............. 424/417, 86, 89; 435/6, 435/69.1, 172.3, 240.21, 240.31, 26; 930/220, 34, 223; 436/71

[56] References Cited

U.S. PATENT DOCUMENTS

| | | | |
|---|---|---|---|
| 3,884,638 | 5/1975 | Dixon et al. | 436/71 |
| 3,954,409 | 5/1976 | Hsia | 436/71 |
| 4,935,363 | 6/1990 | Brown et al. | 435/172.3 |

OTHER PUBLICATIONS

Sigmac Catalogue 1990, pp. 1889–1891, Sigma Chemical Company, Missouri.
Sigma Chemical Co. Catalogue 1990, pp. 305–306, 583, 1303–1323.
Documents Geigy-Scientific Tables, (1970), Diem, K. and Lentner, C. eds. pp. 600–604.
Chen et al., "High-Efficiency Transformation of Mammalian Cells by Plasmid DNA," *Molec. and Cell. Biol.*, 2745–2752 (1987).

*Primary Examiner*—Jacqueline Stone
*Assistant Examiner*—Brian R. Stanton
*Attorney, Agent, or Firm*—Christie, Parker & Hale

[57] ABSTRACT

The present invention relates to a process, a cell culture medium, and a kit for the rapid, high-efficiency transfection of mammalian cells with exogenous DNA. The process comprises incubating a cell culture in the presence of a transfection medium comprising a serum that is different from the serum in the normal growth medium used to grow the cells, and DNA to produce transfected cells. In a preferred embodiment the normal growth medium comprises fetal bovine serum and the transfection medium comprises a serum such as human, calf, horse, lamb, or pig serum. The transfection medium may further comprise an hydroxylated sterol such as 25-hydroxycholesterol.

10 Claims, No Drawings

METHOD FOR MAMMALIAN CELL TRANSFECTION USING 25-HYDROXYCHOLESTEROL

This invention was made with government support under grant HL30568, awarded by The National Institutes of Health. The United States government has certain rights in this invention.

FIELD OF THE INVENTION

The present invention relates to a method for introducing exogenous DNA into mammalian cells by a rapid transfection method which is highly efficient. A kit which provides the components for carrying out the transfections of the present invention is also contemplated by the present invention.

BACKGROUND OF THE INVENTION

In the late 1970's, methods were developed which allowed the introduction and expression of foreign or exogenous DNA into mammalian cells in culture. This technique, known as transfection or transformation, is a powerful method for examining the function and expression of various genes of mammals and many mammalian viruses.

By introducing exogenous DNA of interest into a cell, and monitoring the expression of a gene contained in the DNA, the gene can be analyzed in greater detail than in a cell where it is naturally expressed. For example, mutations and/or deletions of defined regions of a gene can be used to identify DNA elements within the gene that are important for the regulation of its expression. Such studies have lead to the discovery of novel transcriptional regulatory elements for genes as well as various RNA processing and translational signals. In addition, the introduction of an exogenous gene into a cell line can be used to study the effect of that gene on the growth of the cell or the effect of drugs and other agents on the expression of the transfected gene.

Transfection techniques have also been used to isolate genes by transfecting cells with a pool of genomic DNA and selecting the desired cells using genetic complementation techniques. Various mammalian genes, including the chicken thymidine kinase gene, the human hypoxanthine guanine phosphoribosyl-transferase (HPRT) gene, the human thymidylate synthase gene, the human transferrin receptor gene, a human DNA repair gene, and new oncogenes, have been isolated using this technique.

The broad applicability and usefulness of transfecting DNA into mammalian cells has led to the development of a number of protocols for performing transfections, many of which involve the use of either calcium phosphate or DEAE-dextran (or its analogs) as a carrier to promote the uptake of exogenous DNA by cultured mammalian cells. Other methods have used "lipofection" techniques, which incorporate the use of synthetic cationic lipids to effect the transfection. Osmotic shock of the cells or treatment of the cells with lysosomal inhibitors has been used in an attempt to enhance transfection efficiencies. Other attempts to increase the efficiencies have used high-voltage electric pulses to create pores in the cell membranes to increase the efficiency of DNA uptake by the cells.

The transfection efficiencies obtained by these methods are relatively low, ranging from 0.001% to 1%, depending on the cell line used as a recipient. (Transfection efficiency is often expressed as either: the % of cells which have acquired the characteristic conferred by the introduced gene, as may be determined by staining the treated cells; or a measure of the aggregate amount of DNA taken-up by the cells as determined by assaying for a gene product encoded in the transfected DNA.) These low transfection frequencies have limited the application of the technique to a few cell lines which exhibit high transfection efficiencies.

The ability to transfect a wide variety of cell lines, such as those carrying mutations of interest, would facilitate the analyses of the regulatory regions controlling the expression of genes, allow the isolation of genes by genetic complementation, or the cloning of CDNA sequences on the basis of their expression.

Recently, there have been described higher-efficiency transfection techniques which use a modification of the calcium phosphate-mediated transfection method. The modified calcium phosphate-mediated cell-transfection technique is performed in a BES (N,N-bis(2-hydroxyethyl)-2-amino-ethane-sulfonic acid)/phosphate-buffered saline, adjusted to a pH of about 6.9 to 7.0. An equal volume of the BES/phosphate-buffered saline is added to a solution comprising DNA and 0.25M $CaCl_2$, mixed, and incubated for 10 to 20 minutes at room temperature. The DNA/$CaPO_4$ precipitate which forms is then added dropwise to each 60 mm plate of cells incubated in 5 ml of media containing fetal bovine serum (FBS). The cells are initially incubated in an atmosphere of 3%, by volume, $CO_2$ at 35° C. for about 15 to 24 hours (Chen and Okayama, *Molecular and Cellular Biology*, 7, 2745-2752, 1987). With this transfection method, cells are grown in 10%, by volume, FBS during the transfection procedure. Under these conditions, many common cultured mammalian cell lines have reportedly been transfected with efficiencies as high as 10 to 50%. It should be noted that the results for determining transfection efficiencies reported from this method required long growth periods of the cells prior to quantification, thus allowing "daughter" cells from the originally transfected cells to "reseed" the plate, resulting in an artificially high measure of transfection efficiency.

While such techniques represent an improvement over the previously known techniques, it is desirable that a transfection method is provided which results in higher transfection efficiencies, as determined by the number of cells which take up DNA and the amount of DNA taken up by the cells. It is also desirable that the time taken to perform the transfection procedure is reduced so that results of the transfection can be evaluated in a shorter time period than is currently required.

In view of the foregoing, there is a need for a method of transfecting cells which results in high transfection efficiencies, with a wide variety of mammalian host cell lines, and which requires only a short period of time for cells to take up exogenous DNA.

SUMMARY OF THE INVENTION

The present invention relates to a process for high-efficiency transfection of mammalian cells. The process comprises incubating a cell culture in the presence of a transfection medium comprising a serum such as human, calf, horse, lamb, or pig serum, and DNA to produce transfected cells, wherein the serum in the transfection medium is different from the serum used to grow the cells.

More specifically, the process comprises growing mammalian cells in a growth medium comprising a first serum such as FBS, then transferring the cells to a transfection medium comprising a second serum, which is not FBS, such as human, calf, horse, lamb, or pig serum, then adding a calcium phosphate-DNA precipitate solution to the medium over the cells, to form a calcium phosphate-DNA precipitate/medium mixture. The transfection medium may further comprise an hydroxylated sterol such as 25-hydroxycholesterol.

The present invention also relates to a medium for transfecting mammalian cells which comprises a serum that is not FBS, such as human, calf, horse, lamb, or pig serum. The medium may further comprise an hydroxylated sterol such as 25-hydroxycholesterol.

Also contemplated by the present invention is a kit for the transfection of mammalian cells comprising a transfection medium which comprises a serum that is not FBS, such as human, calf, horse, lamb, or pig serum. The kit may further comprise an hydroxylated sterol such as 25-hydroxycholesterol.

DETAILED DESCRIPTION

In the present invention, cells are stably or transiently transfected with exogenous DNA under conditions which include the use of a calcium phosphate-DNA precipitate added to cells in a transfection medium. The transfection medium of the present invention comprises a serum that is different from the serum used in the growth medium, which is used to grow the cells. During the transfection procedure, the cells are incubated at a temperature of about 35° C. to about 37° C., and in an atmosphere of about 2% to about 5%, by volume, $CO_2$. After a short incubation period (about 3 to about 4 hours), during which the cells take up the DNA, the cells are transferred to a growth medium and are incubated at 37° C. in an atmosphere of about 5%, by volume, $CO_2$. In a preferred embodiment of the present invention, the transfection medium comprises about 10%, by volume, of a serum which is not FBS and about 2.5 μg/ml of an hydroxylated sterol such as 25-hydroxycholesterol. These transfection conditions result in a rapid and efficient uptake of the exogenous DNA by the host cell lines.

Transfection of Cells

Mammalian cells capable of growth in culture are suitable for use in the present invention. Preferably, the cells are adapted to growing in monolayers. For use in the present invention, cells, growing exponentially, are harvested by trypsinization or by other techniques that are well known in the art. The harvested cells are then plated onto sterile 60-mm plates and incubated until the cell cultures are about 20% to about 90% confluent. While 60-mm plates are preferred in the present invention (since they are easy to manipulate), other-sized plates could also be used. About 5 ml of a standard growth medium, such as Ham's F12 medium comprising about 10% FBS, is added to the 60-mm plates containing the cells, and the cells are incubated overnight (about 18 to about 20 hours), at about 37° C. in an atmosphere of about 5%, by volume, $CO_2$, to allow them to attach to the surface of the plates.

The medium used to grow or transfect the cells is one that is appropriate for the cells being cultured. Such media are well known in the art, and one of ordinary skill in the art would be familiar with media appropriate for growing the cells chosen to be cultured. For example, CV1 cells (American Type Culture Collection (ATCC) No. CCL70, Rockville, Md.) and mouse F9 cells (ATCC No. CRL1720) may be grown in Dulbecco modified Eagle medium (DMEM), supplied by GIBCO of Grand Island, N.Y.; CHO-K1 cells (ATCC No. CCL61), HepG2 cells (ATCC No. HB8065), murine L cells (ATCC No. CCL1), and human Caco-2 cells (ATCC No. HTB37) may all be grown in α-MEM or Ham's F12 medium, supplied by GIBCO; and P3X63-AG8.653 cells (ATCC No. CRL1580) may be grown in RPMI 1640 medium, also supplied by GIBCO.

Preferably, the normal growth medium used in accordance with the present invention comprises about 5% to about 20%, by volume, of a first serum, such as FBS supplied by Gemini of Calabasas, Calif. Most preferably, the medium comprises about 10%, by volume, FBS.

Antibiotics and fungicides may be added to the medium to prevent the growth of bacteria and fungi in the cell cultures. Antibiotics suitable for use in the practice of the present invention are those such streptomycin, penicillin, and fungizone (which are supplied by Whittacker Bioproducts of Walkersville, Md., as a 100-fold concentrate which is diluted 1:100 for use), although other antibiotics known in the art may also be used. These antibiotics may be added to all media preparations.

At the completion of the overnight incubation, the growth medium is removed from the cells and the cells are washed about twice with phosphate buffered saline (PBS). A transfection medium comprising about 5% to about 20%, by volume, of a second serum, which is different from the first serum, such as human, calf, horse, lamb, or pig serum, is then added to the cells. Preferably, if human serum is used in the transfection medium, the blood from which the human serum is derived is drawn from fasted individuals, to reduce the concentration of lipids present in the blood. The serum may be whole serum, lipoprotein deficient fraction of serum (LPDS), or other suitable serum fractions, serum components, or "synthetic serum" compositions. Most preferably, the transfection medium comprises about 10%, by volume, of the serum.

In a preferred embodiment of the present invention, the transfection medium also comprises about 0.1 μg/ml to about 5 μg/ml of a hydroxylated sterol to enhance the uptake of DNA by the cells. At a concentration below about 0.1 μg/ml, the beneficial effect of the hydroxylated sterol on increasing the efficiency of transfection is minimal; above a concentration of about 5 μg/ml, little additional increase in the efficiency of transfection is observed. Most preferably, the medium comprises about 2.5 μg/ml of hydroxylated sterol. In the present invention 25-hydroxycholesterol is preferred.

A calcium phosphate-DNA precipitate solution is added to the transfection medium. The calcium phosphate-DNA precipitate solution is prepared by mixing about 20 to about 30 μg of plasmid DNA with about 0.5 ml of about 250 mM $CaCl_2$ (such as that supplied by Sigma Chemical Co. of St Louis Mo., or J. T. Baker Chemical Co. Phillipsburg, N.J.). The $CaCl_2$ solution is sterilized by filtering it through a filter such as a 0.45-μm-pore-size nitrocellulose filter, supplied by Nalge of Rochester, N.Y., or by other suitable sterilization methods.

About 0.5 ml of a solution comprising about 50 mM of a buffer such as N,N-bis(2-hyroxyethyl)-2-aminoethane-sulfonic acid (BES) (supplied by Sigma Chemical Co.), adjusted with HCl to about pH 6.9 to about 7.0, about 280 mM NaCl, and about 1.5 mM $Na_2HPO_4$ (sterilized as described above), is added to the DNA-$CaCl_2$ solution, and the resultant mixture is incubated for about 10 to about 30 minutes at room temperature to form a calcium phosphate-DNA precipitate solution. The exact pH to be used is tested for each BES solution prepared and for each cell line to be transfected.

The final concentration of the components in the calcium phosphate-DNA precipitate solution is about 20 to about 30 µg/ml of plasmid DNA, about 125 mM CaCl, about 25 mM BES, adjusted to a pH of about 6.9 to about 7.0, about 140 mM NaCl, and about 0.75 mM $Na_2HPO_4$. It is preferable that the two components of the mixture (i.e., the DNA-$CaCl_2$ and the BES-NaCl-$Na_2HPO_4$) are made up separately and then added together to promote formation of a calcium phosphate-DNA precipitate.

DNA for use in the present invention is preferably circular DNA, since transfection efficiencies are higher with circular DNA than with linear DNA. The DNA is preferably a plasmid which comprises the gene of interest, and may also comprise a marker gene, such as the $\beta$-galactosidase gene (the *E. coli* lac Z gene). The inclusion of a marker gene is convenient for assaying for transfection efficiency, since the presence of the gene product, in this case $\beta$-galactosidase ($\beta$-gal), may be easily assayed enzymatically or by staining. The relative activity of this enzyme produced by the transfected cells is proportional to the efficiency of transfection.

Additionally, the plasmid may contain a gene which is a selectable marker. For example, the "neo" gene (which confers resistance to the drug G418) may be included in the transfection. The presence and expression of such genes allows the selection of cells, which have taken up DNA, by growing them in a selection medium.

A gene to complement a mutation present in the mammalian host cells may also be used as a means of selecting particular transfectants. Such complementation assays are well known to those skilled in the art.

The plasmid may also comprise a gene in the form of a cDNA copy of any desired gene.

For use in the present invention, the genes to be transfected may be incorporated into a single plasmid or they may be incorporated into separate plasmids. Where the genes of interest are incorporated into separate plasmids, the plasmids are mixed and transfected together as a single plasmid sample.

The construction of plasmids containing desired genes is well known to those skilled in the art, and any such method of constructing plasmids is suitable for use in the present invention.

Such plasmid DNA may then be grown in suitable host cells such as *Escherichia coli* (*E. coli*). The plasmid DNA may be isolated from the host cells by any of the methods known in the art which result in the purification of circular DNA. The purified plasmid is preferably extracted extensively with phenol, chloroform, and ether, to ensure that no *E. coli* proteins are present in the plasmid DNA preparation, since these proteins are often toxic to mammalian cells.

About 0.5 ml of the calcium phosphate-DNA precipitate solution is added, dropwise, to the transfection medium (comprising the second serum) on each plate of cells to be transfected, and the mixture is swirled gently. The cells are then incubated for about 2 to about 4 hours, at about 35° C., in an atmosphere of about 2% to about 4%, by volume, $CO_2$, and preferably in an atmosphere of about 3%, by volume, $CO_2$, to allow the cells to take up the DNA from the calcium phosphate-DNA precipitate.

At the end of the incubation, the transfection medium comprising the second serum is removed and the cells are rinsed with PBS. Preferably, the rinsing is performed about twice. About 5 ml of the growth medium is added to the cells, and the cells are then incubated for about 15-24 hours, at about 37° C. in an atmosphere of about 5%, by volume, $CO_2$. The cells are then harvested and assayed for the presence of marker gene-product.

The process of the present invention results in relative transfection efficiencies that are as much as 20- to 2,000-fold higher than those obtained by other transfection procedures. The increased relative transfection efficiency of the present invention appears, from histochemical studies, to result from an increase in the number of cells which take up DNA and from an increased amount of DNA taken up by the cells. Additionally, the time required for the uptake of the DNA is reduced to about 2 to about 4 hours, and protein produced by the marker genes transfected into the cells may be assayed within about 18 to about 20 hours after the transfection procedure. In contrast, other transfection methods require about 6 to about 24 hours for the cells to take up DNA, after which time a period of at least an additional 24 to 72 hours is required before marker genes can be selected or assayed. Therefore, the process of the present invention results in a reduction of up to 48 hours in the total time required to perform a transfection and to measure transfection efficiencies.

Transfection Kit

Also contemplated by the present invention is a kit for the transfection of mammalian cells. Such a kit comprises the components required to conduct the transfection assay. Each of the components is supplied in a separate container, as follows:

1. A concentrated transfection medium supplement, comprising about 100%, by volume, serum that is not FBS, such as human, calf, horse, lamb, or pig serum. The supplement is diluted about ten-fold for use in medium. While a supplement requiring a 1:10 dilution is convenient for use in the present invention, lower concentrations, requiring lower dilution, may also be used.

2. A concentrated transfection medium supplement, comprising about 2.5 mg/ml of an hydroxylated sterol such as 25-hydroxycholesterol in ethanol. Preferably, the transfection medium is supplemented with about 2.5 µg/ml 25-hydroxycholesterol. The concentrated supplement is diluted 1,000-fold for use in medium. While a supplement requiring a 1:1,000 dilution is convenient for use in the present invention, higher or lower concentrations, requiring higher or lower dilution, may also be used. However, since ethanol is toxic to the cells at high concentrations, it is desirable that the final ethanol concentration in the transfection medium is relatively low.

3. A solution comprising sterile 250 mM $CaCl_2$. The $CaCl_2$ solution may be supplied as a sterile concentrate of about 2.5M, if preferred. If the $CaCl_2$ is supplied as a concentrate, it is diluted ten-fold for use. A concentrate may be preferred if large volumes of plasmid DNA are to be used. Under these conditions, for one transfection experiment, the dilute plasmid DNA is added to a container, and about 0.05 ml of the concentrated CaCl₂ is added. The volume of the mixture is then brought to 0.5 ml by the addition of sterile, distilled water.

If concentrated solutions of plasmid DNA are used, however, the DNA may be added directly to a diluted CaCl₂ sample, since the additional volume of the DNA sample is insignificant.

4. A solution comprising sterile 50 mM N,N-bis(2-hydroxyethyl)-2-aminoethane-sulfonic acid (BES), about 280 mM NaCl, and about 1.5 mM Na₂HPO₄. The pH of the solution is adjusted, prior to use, to a pH of about 6.9 to about 7.0.

5. Control plasmid DNA solutions, which are known to give high transfection efficiency in certain cell types, may be provided for testing and comparing the efficiency of transfection.

6. Assay reagents to assay the marker gene product incorporated into the plasmid DNA.

Kits prepared in accordance with the present invention may include all the components listed above or only a few of the components which would not normally be purchased by a laboratory conducting transfection experiments. However, the kit will include at least the transfection-medium supplement comprising a serum that is not FBS, such as human, calf, horse, lamb or pig serum.

EXAMPLE 1

Isolation of Plasmid DNA

The plasmid used in the following experiments was a β-gal-containing plasmid designated pON260, which comprises the cytomegalovirus promoter described by Boshart et al. in *Cell*, 41, 521–531 (1985), the β-gal gene of *E. coli*, and the polyadenylation sequence from the SV40 late region, inserted into pBR322.

300 μl of an overnight culture of *E. coli*, which includes the pON260 plasmid containing the β-gal gene, was added to 25 ml of Luria Broth and was grown, at 37° C., to an optical density, at 550 nm, of 0.6. Ten ml of this culture was then added to one liter of Luria Broth supplemented with ampicillin (100 μg/ml), and the culture was grown overnight, at 37° C., with shaking at 250 rpm.

The cells were collected by centrifugation at 7,000 rpm for 20 min. at 4° C. The resultant pellet was resuspended in 80 ml of 10% (wt/vol) sucrose, 50 mM Tris-HCl, pH 8.0. Once the cells were resuspended, 8 ml of 10 mg/ml lysozyme in 0.25 M Tris-HCl (pH 8.0), 16 ml of water, and 16 ml of 0.5M EDTA were added to the cell suspension. The mixture was incubated on ice for 15 min. At the end of the incubation, 16 ml of 10% (wt/vol) SDS was added, dropwise, as the cell suspension was gently swirled. The solution was incubated on ice for about 2 hours, with shaking. At the end of the incubation, the mixture was centrifuged at 17,000 rpm for 15 min. at 4° C. The supernatant was collected and filtered through cheesecloth, and 1 volume of 5M NaCl was added for each 4 volumes of supernatant. The mixture was then incubated on ice for 2 hrs., with shaking. Particulate matter was removed by centrifugation at 13,000 rpm for 25 min. at 4° C., and the resultant supernant was filtered through cheesecloth. The DNA contained in the filtered supernatant was precipitated by adding 2 volumes of ethanol and incubating overnight at −70° C. The DNA precipitate was collected by centrifugation at 8,000 rpm for 20 min. at 4° C.

The DNA pellet was resuspended in a final, total volume of 17 ml of 10 mM Tris-HCl, pH 7.5, and 1 mM EDTA. 1.02 g of CsCl per ml of solution was added, as was 0.05 ml of 10 mg/ml of ethidium bromide, and the solution was mixed until the CsCl was dissolved. The solution was checked to ensure that the refractive index after the addition of the CsCl and ethidium bromide was 1.396. The CsCl/ethidium bromide/DNA solution was centrifuged at 35,000 rpm for 48 to 60 hrs. at 20° C. The DNA band was collected and extracted four times with sec-butanol, saturated with CsCl, to remove the ethidium bromide from the DNA. The extracted DNA was precipitated by adding one volume of water and four volumes of ethanol and incubating overnight at −20° C. The precipitated DNA was collected by centrifugation at 8,000 rpm for 30 min. at 0° C.

The precipitate was resuspended in 10 mM Tris-HCl, pH 7.5, and 1 mM EDTA and extracted as follows: once with phenol, twice with phenol:chloroform (1:1), once with chloroform, and twice with ether. The extracted DNA was precipitated by adding a 0.5 volume of 7.5M ammonium acetate and 2.5 volumes of ethanol and incubating overnight at −20° C. The precipitate was collected by centrifugation at 8,000 rpm for 20 min. at 0° C., and was resuspended in 400 μl of 10 mM Tris-HCl, pH 7.5, and 1 mM EDTA.

The DNA was then reprecipitated by adding a 0.5 volume of 7.5M ammonium acetate and 2.5 volumes of ethanol and incubating overnight at −20° C. The precipitate was collected by centrifugation at 8,000 rpm for 20 min. at 0° C., and was resuspended in 500 μl of 10 mM Tris-HCl, pH 7.5, and 1 mM EDTA.

The plasmid DNA was then used in transfection experiments.

EXAMPLE 2

Control Transfection of CHO Cells with βgal Plasmid in the Presence of 10% Fetal Bovine Serum in Ham's F12 Medium (Chen-Okayama Method)

Monolayers of CHO cells, growing exponentially in Ham's F12 medium supplemented with 10%, by volume, FBS were harvested by trypsinization. The cells were then plated in duplicate onto sterile 60-mm culture plates and incubated in 5 ml of Ham's F12 medium supplemented with 10%, by volume, FBS, until the cell cultures were about 50% confluent.

After the incubation (usually 16–24 hrs.), the medium was removed, the cells were washed twice with PBS, and 5 ml of Ham's F12 medium supplemented with 10%, by volume, FBS was added to the cells.

25 μg of plasmid DNA, 8 μg of which was a β-gal-containing plasmid, prepared by the method described in Example 1, was mixed with 0.5 ml of 250 mM CaCl₂. 0.5 ml of 50 mM BES (pH 6.96), 280 mM NaCl, and 1.5 mM Na₂HPO₄ were added to the DNA-CaCl₂ solution, and the resultant mixture was incubated, for not less than 10 but not more than 30 minutes, at room temperature, to form a calcium phosphate-DNA precipitate solution. The time difference in the incubation to form the calcium phosphate-DNA precipitate solution is due to the time required to add the solution to each of the individual cultures to be transfected as described below.

0.5 ml of the calcium phosphate-DNA precipitate solution was then added, dropwise, to each plate of cells, and the calcium phosphate-DNA precipate/medium mixture was swirled gently. The plates were incubated for 3 to 4 hours at 35° C. in an atmosphere of 3%, by volume, CO₂. At the end of the incubation, the Ham's F12 medium supplemented with 10% FBS was removed and the cells were rinsed at least twice with PBS. Five ml of Ham's F12 medium supplemented with 10%, by volume, FBS was added to the cells and the cells were incubated at 37° C. in an atmosphere of 5%, by volume, $CO_2$. The following day (about 18 to 24 hours post-transfection), the cells were harvested, lysed by multiple freeze-thaw cycles, and centrifuged at 10,000 rpm for 10 min. The supernatant was assayed for β-gal activity.

The β-gal activity was assayed by adding 100 μl of supernatant of 900 μl of a solution comprising 100 mM sodium phosphate, pH 7.5, 10 mM KCl, 1 mm $MgSO_4$, and 50 mM β-mercaptoethanol. After the mixture had been incubated at 37° C. for 5 min., 200 μl of 4 mg/ml O-nitrophenyl β-D-galactapyranoside, dissolved in 100 mm sodium phosphate (pH 7.5), was added and the solution was mixed. The solution was incubated at 37° C. until a bright yellow color developed. At that time, the reaction was terminated by the addition of 500 μl of 1M $Ca_2O_2$. The adsorbance of the samples was then read at 420 nm. The results are shown in Table I.

EXAMPLE 3

Transfection of CHO Cells with β-gal Plasmid in the Presence of 5.8% Human Lipoprotein Deficient Serum (LPDS)

Monolayers of CHO cells, growing exponentially in Ham's F12 medium supplemented with 10%, by volume, FBS were harvested by trypsinization. The cells were then plated, to about 50% confluence, in duplicate sterile 60 mm culture plates and incubated overnight in 5 ml of Ham's F12 medium supplemented with 10%, by volume, FBS.

After the incubation, the medium was removed, the cells were washed twice with PBS, and 5 ml of Ham's F12 supplemented with 5.8% LPDS was added to the cells.

The remainder of the transfection procedure was as described in Example 2. The results are shown in Table I.

EXAMPLE 4

Transfection of CHO Cells with β-gal Plasmid in the Presence of 5.8% Human LPDS and 1 μg/ml of 25-Hydroxycholesterol/10 μg/ml Cholesterol Mixture (25-HC/C)

The procedure was the same as described in Example 3, except the transfection was performed in the presence of Ham's F12 supplemented with 5.8%, by volume, human LPDS, 1 μg/ml 25-hydroxycholesterol, and 10 μg/ml cholesterol. The results are shown in Table I.

TABLE I

| Example | Medium | β-gal Activity[1] | Rel. Transfec. Efficiency[2] |
|---|---|---|---|
| 2[3] | Ham's F12 + FBS | 42 | 1 |
| 3 | Ham's F12 + LPDS | 1,375 | 33 |
| 4 | Ham's F12 + LPDS + 25-HC/C[4] | 3,462 | 82 |

[1] nmoles of o-nitrophenol formed per min. per mg of protein
[2] relative transfection efficiency is calculated by dividing the units of β-gal activity in the test sample by the units of β-gal activity in the control (the transfection performed with medium supplemented with 10% by volume FBS)
[3] control
[4] 25-hydroxycholesterol/cholesterol mixture The results indicate that the addition of 5.8%, by volume, human LPDS in place of the 10%, by volume, FBS normally used in transfection procedures, results in a 33-fold increase in relative transfection efficiency. This efficiency is furthered to an 82-fold increase by also supplementing the medium with 1 μg/ml of 25-hydroxycholesterol and 10 μg/ml cholesterol.

EXAMPLE 5

Transfection of CHO Cells with β-gal Plasmid Using 10% FBS in Ham's F12 Medium (Control)

The procedure described in Example 2 was repeated. The results are shown in Table II.

EXAMPLE 6

Transfection of CHO Cells with β-gal Plasmid Using 5.8% Human LPDS in Ham's F12 Medium and 1 μg 25-hydroxycholesterol/ 10 μg/ml Cholesterol (25-HC/C).

The procedure described in Example 4 was repeated. The results are shown in Table II.

EXAMPLE 7

Transfection of CHO Cells with β-gal Plasmid Using 10% Human Serum (HS) in Ham's F12 Medium The procedure described in Example 3 was repeated except human serum was used in place of LPDS. The results are shown in Table II.

EXAMPLE 8

Transfection of CHO Cells With β-gal Plasmid Using 10% HS in Ham's F12 Medium and 1 μg 25-hydroxycholesterol/ 10 μg/ml Cholesterol (25-HC/C)

The procedure described in Example 4 was repeated except that the transfection was performed in the presence of Ham's F12 supplemented with 10%, by volume, human serum, 1 μg/ml 25-hydroxycholesterol, and 10 μg/ml cholesterol. The results are shown in Table II.

TABLE II

| Example | Medium | β-gal Activity[1] | Rel. Transfec. Efficiency[2] |
|---|---|---|---|
| 5[3] | Ham's F12 + FBS | 7 | 1 |
| 6 | Ham's F12 + LPDS + 25-HC/C[4] | 512 | 72 |
| 7 | Ham's F12 + HS | 386 | 54 |
| 8 | Ham's F12 + HS + 25-HC/C | 1,034 | 146 |

[1] nmoles of o-nitrophenol formed per min. per mg of protein
[2] relative transfection efficiency is calculated by dividing the units of β-gal activity in the test sample by the units of β-gal activity in the control (the transfection performed with medium supplemented with 10% by volume FBS).
[3] control
[4] 25-hydroxycholesterol/cholesterol mixture The results show that the use of human serum results in an increase in the transfection efficiency over media supplemented with 10% FBS. This high efficiency of transfection is further increased by the addition of 1 μg/ml 25-hydroxycholesterol and 10 μg/ml cholesterol.

EXAMPLE 9

Effect of Incubation Time on Transfection Efficiency (Control)

The procedure described in Example 2 was repeated. The results are shown in Table III.

EXAMPLE 10

Effect of Incubation Time on Transfection Efficiency

The procedure described in Example 7 was repeated, except the cells were incubated in the presence of the calcium phosphate-DNA precipitate/medium mixture for 1 hour instead of 3 hours. The results are shown in Table III.

EXAMPLE 11

Effect of Incubation Time on Transfection Efficiency

The procedure described in Example 7 was repeated except the cells were incubated in the presence of the calcium phosphate-DNA precipitate/medium mixture for 2 hours instead of 3 hours. The results are shown in Table III.

EXAMPLE 12

Effect of Incubation Time on Transfection Efficiency

The procedure described in Example 7 was repeated. The results are shown in Table III.

EXAMPLE 13

Effect of Incubation Time on Transfection Efficiency

The procedure described in Example 7 was repeated except the cells were incubated in the presence of the calcium phosphate-DNA precipitate/medium mixture for 4 hours instead of 3 hours. The results are shown in Table III.

TABLE III

| Ex. | Medium | Inc. time w/calc. phos.-DNA | $\beta$-gal Activity[1] | Rel. Transfec. Efficiency[2] |
| --- | --- | --- | --- | --- |
| 9[3] | Ham's F12 + FBS | 3 | 12 | 1 |
| 10 | Ham's F12 + HS | 1 | 114 | 10 |
| 11 | Ham's F12 + HS | 2 | 1,326 | 111 |
| 12 | Ham's F12 + HS | 3 | 3,535 | 295 |
| 13 | Ham's F12 + HS | 4 | 4,090 | 241 |

[1] nmoles of o-nitrophenol formed per min. per mg of protein
[2] relative transfection efficiency is calculated by dividing the units of $\beta$-gal activity in the test sample by the units of $\beta$-gal activity in the control (the transfection performed with medium supplemented with 10% by volume FBS).
[3] control The results indicate that transfection is increased as the incubation time, in the presence of the calcium phosphate-DNA precipitate/medium mixture, is increased; although high levels of transfection are observed with only 2 hours of incubation.

EXAMPLE 14

Effect of Concentration of 25-Hydroxycholesterol on Transfection Efficiency (Control)

The procedure described in Example 2 was repeated. The results are shown in Table IV.

EXAMPLE 15

Effect of Concentration of 25-Hydroxycholesterol on Transfection Efficiency

The procedure described in Example 7 was repeated. The results are shown in Table IV.

EXAMPLE 16

Effect of Concentration of 25-Hydroxycholesterol on Transfection Efficiency

The procedure described in Example 7 was repeated, except 0.1 $\mu$g/ml of 25-hydroxycholesterol was added to the transfection medium in place of the 1 $\mu$g/ml hydroxycholesterol/10 $\mu$g/ml cholesterol. The results are shown in Table IV.

EXAMPLE 17

Effect of Concentration of 25-Hydroxycholesterol on Transfection Efficiency

The procedure described in Example 16 was repeated, except 0.5 $\mu$g/ml of 25-hydroxycholesterol was added to the transfection medium. The results are shown in Table IV.

EXAMPLE 18

Effect of Concentration of 25-Hydroxycholesterol on Transfection Efficiency

The procedure described in Example 16 was repeated, except 1.0 $\mu$g/ml of 25-hydroxycholesterol was added to the transfection medium. The results are shown in Table IV.

EXAMPLE 19

Effect of Concentration of 25-Hydroxycholesterol on Transfection Efficiency

The procedure described in Example 16 was repeated, except 2.5 $\mu$g/ml of 25-hydroxycholesterol was added to the transfection medium. The results are shown in Table IV.

EXAMPLE 20

Effect of Concentration of 25-Hydroxycholesterol on Transfection Efficiency

The procedure described in Example 16 was repeated, except 5.0 $\mu$g/ml of 25-hydroxycholesterol was added to the transfection medium. The results are shown in Table IV.

EXAMPLE 21

Effect of Concentration of 25-Hydroxycholesterol on Transfection Efficiency

The procedure described in Example 16 was repeated, except 10.0 $\mu$g/ml of 25-hydroxycholesterol was added to the transfection medium. The results are shown in Table IV.

TABLE IV

| Ex. | Medium | 25-Hydroxycholest. $\mu$g/ml | $\beta$-gal Activity[1] | Rel. Transfec. Efficiency[2] |
| --- | --- | --- | --- | --- |
| 14[3] | Ham's F12 + FBS | 0 | 1.5 | 1 |
| 15 | Ham's F12 + HS | 0 | 76 | 51 |
| 16 | Ham's F12 + HS | 0.1 | 231 | 154 |
| 17 | Ham's F12 + HS | 0.5 | 518 | 346 |
| 18 | Ham's F12 + HS | 1 | 973 | 649 |
| 19 | Ham's F12 + HS | 2.5 | 1,385 | 923 |
| 20 | Ham's F12 + HS | 5 | 1,451 | 967 |
| 21 | Ham's F12 + HS | 10 | 1,465 | 977 |

[1] nmoles of o-nitrophenol formed per min. per mg of protein
[2] relative transfection efficiency is calculated by dividing the units of $\beta$-gal activity in the test sample by the units of $\beta$-gal activity in the control (the transfection performed with medium supplemented with 10% by volume FBS).
[3] control The results indicate that 2.5 $\mu$g/ml of 25-hydroxycholesterol added to Ham's medium supplemented with 10% human serum results in optimum transfection efficiencies.

EXAMPLE 22

Comparison of Different Transfection Methods (Control)

The procedure described in Example 2 was repeated. The results are shown in Table V.

EXAMPLE 23

Comparison of Different Transfection Methods

The procedure described in Example 19 was repeated. The results are shown in Table V.

EXAMPLE 24

Comparison of Different Transfection Methods

The procedure described in Example 19 was repeated, except the human serum used in the procedure was from a different donor. The results are shown in Table V.

EXAMPLE 25

Comparison of the Different Transfection Methods

Monolayers of CHO cells, growing exponentially in Ham's F12 medium supplemented with 10%, by volume, FBS were harvested by trypsinizing. The cells were then plated, to 50% confluence, in duplicate sterile 60-mm culture plates and incubated overnight in 5 ml of Ham's F12 medium supplemented with 10%, by volume, FBS.

After the incubation, the medium was removed and the cells were washed twice with 3 ml OPTIMEM (supplied by GIBCO), and 3 ml of OPTIMEM was added to the cells.

15.0 μg of plasmid DNA, 4 μg of which was a β-gal-containing plasmid, prepared as described in Example 1, was diluted to 50 μl with water. Forty μg LIPOFECTIN (supplied by GIBCO) was diluted with an equal volume of water. The DNA and LIPOFECTIN solutions were mixed, incubated for 15 min. at room temperature, and added, dropwise, to each plate of cells. The LIPOFECTIN-DNA precipitate mixture was swirled gently, and the plates were incubated for 6 hours at 37° C. in an atmosphere of 5%, by volume, $CO_2$. At the end of the incubation, the LIPOFECTIN-DNA precipitate mixture was removed. Five ml of Ham's F12 medium supplemented with 10%, by volume, FBS was added to the cells, and the cells were then incubated for 48 hours at 37° C. in an atmosphere of 5%, by volume, $CO_2$. The cells were harvested, lysed by multiple freeze-thaw cycles, centrifuged, and assayed for β-gal activity. The β-gal assays were performed as described in Example 2. The results are shown in Table V.

EXAMPLE 26

Comparison of Different Transfection Methods

The procedure described in Example 25 was repeated, except 35 μg of LIPOFECTIN was added instead of 40 μg. The results are shown in Table V.

EXAMPLE 27

Comparison of Different Transfection Methods

The procedure described in Example 25 was repeated, except 30 μg of LIPOFECTIN was added instead of 40 μg. The results are shown in Table V.

TABLE V

| Example | Medium | β-gal Activity[1] | Rel. Transfec. Efficiency[2] |
|---|---|---|---|
| 22[3] | Ham's F12 + FBS | 1.5 | 1 |
| 23 | Ham's F12 + HS + 25-HC | 3030 | 2020 |
| 24 | Ham's F12 + HS + 25-HC | 1236 | 824 |
| 25 | Ham's F12 + FBS + 40 μg/ml LIPOFECTIN | 25 | 17 |
| 26 | Ham's F12 + FBS + 35 μg/ml LIPOFECTIN | 47 | 31 |
| 27 | Ham's F12 + FBS + 30 μg/ml LIPOFECTIN | 79 | 53 |

[1]nmoles of o-nitrophenol formed per min. per mg of protein
[2]relative transfection efficiency is calculated by dividing the units of β-gal activity in the test sample by the units of β-gal activity in the control (the transfection performed with medium supplemented with 10% by volume FBS).
[3]control Transfections in the presence of LIPOFECTIN were found to be less efficient than with Ham's F12 in the presence of 10% human serum and 2.5 μg/ml 25-hydroxycholesterol.

EXAMPLE 28

Transfection with Human Hepatoma (Hep G2) Cells (Control)

The procedure described in Example 2 was repeated except human hepatoma cells were used in place of CHO cells, the cells were grown in minimal essential media (MEM) (supplied by GIBCO), and 15 μg of plasmid DNA, 8 μg of which was a β-gal-containing plasmid, was transfected into each plate of Hep G2 cells. The results are shown in Table VI.

EXAMPLE 29

Transfection with Human Hepatoma (Hep G2) Cells

The procedure described in Example 3 was repeated, except human hepatoma cells were used in place of CHO cells, the cells were grown in minimal essential media (MEM) (supplied by GIBCO), and 15 μg of plasmid DNA, 8 μg of which was a β-gal-containing plasmid, was transfected into each plate of Hep G2 cells. The results are shown in Table VI.

EXAMPLE 30

Transfection with Human Hepatoma (Hep G2) Cells

The procedure described in Example 4 was repeated, except human hepatoma cells were used in place of CHO cells, the cells were grown in minimal essential media (MEM) (supplied by GIBCO), and 15 μg of plasmid DNA, 8 μg of which was a β-gal-containing plasmid, was transfected into each plate of Hep G2 cells. The results are shown in Table VI.

TABLE VI

| Example | Medium | β-gal Activity[1] | Rel. Transfec. Efficiency[2] |
|---|---|---|---|
| 28[3] | MEM + FBS | 0.53 | 1 |
| 29 | MEM + LPDS | 7.17 | 14 |
| 30 | MEM + LPDS + 25-HC/C[4] | 12.3 | 23 |

[1]nmoles of o-nitrophenol formed per min. per mg of protein
[2]relative transfection efficiency is calculated by dividing the units of β-gal activity in the test sample by the units of β-gal activity in the control (the transfection performed with medium supplemented with 10% by volume FBS).
[3]control
[4]25-hydroxycholesterol/cholesterol mixture The results indicate that higher transfection efficiencies in Hep G2 cells are obtained with the use of MEM supplemented with LPDS than with MEM supplemented with FBS. Increased transfection efficiencies are obtained when the medium is supplemented with 25-HC/C.

EXAMPLE 31

Transfection with Murine L Cells (Fibroblasts) (Control)

The procedure described in Example 2 was repeated, except murine L cells were used in place of CHO cells. The results are shown in Table VII.

EXAMPLE 32

Transfection with Murine L Cells (Fibroblasts)

The procedure described in Example 3 was repeated, except murine L cells were used in place of CHO cells. The results are shown in Table VII.

TABLE VII

| Example | Medium | $\beta$-gal Activity[1] | Rel. Transfec. Efficiency[2] |
|---|---|---|---|
| 31[3] | Ham's F12 + FBS | 0.99 | 1 |
| 32 | Ham's F12 + LPDS | 22.1 | 22 |

[1] nmoles of o-nitrophenol formed per min. per mg of protein
[2] relative transfection efficiency is calculated by dividing the units of $\beta$-gal activity in the test sample by the units of $\beta$-gal activity in the control (the transfection performed with medium supplemented with 10% by volume FBS)
[3] control The results indicate that higher transfection efficiencies in Murine L cells are obtained with the use of Ham's F12 in the presence of 5.8% human LPDS than in the presence of 10% FBS.

EXAMPLE 33

Comparison of FBS and LPDS on Transfection Efficiency Using the "Standard CaPO$_4$ Transfection Method"

CHO cells were transfected by the "standard CaPO$_4$ transfection method" described in "Transfection DNA into Eukaryotic Cells" in: Current Protocols in Molecular Biology, Vol. 1 (Ausubel et al., eds.), Wiley Interscience, pp. 9.1.1-9.1.3, incorporated herein by this reference. A $\beta$-gal-containing plasmid, prepared by the method described in Example 1, was used in the transfections, in which FBS was used in the growth medium as well as in the transfection medium. The results are shown in Table VIII.

EXAMPLE 34

Comparison of FBS and LPDS on Transfection Efficiency Using the "Standard CaPO$_4$ Transfection Method"

The method of Example 33 was repeated, except LPDS was used in place of FBS in the growth medium. The results are shown in Table VIII.

EXAMPLE 35

Comparison of FBS and LPDS on Transfection Efficiency Using the "Standard CaPO$_4$ Transfection Method"

The method of Example 33 was repeated, except LPDS was used in place of FBS in the growth and transfection medium. The results are shown in Table VIII.

EXAMPLE 36

Comparison of FBS and LPDS on Transfection Efficiency Using the "Standard CaPO$_4$ Transfection Method"

The method of Example 33 was repeated, except LPDS was used in place of FBS in the transfection medium. The results are shown in Table VIII.

TABLE VIII

| Example | Transfec. Serum | Growth Serum | $\beta$-gal Activity[1] |
|---|---|---|---|
| 33[2] | FBS | FBS | 36.1 |
| 34 | FBS | LPDS | 36.1 |
| 35 | LPDS | LPDS | 481 |
| 36 | LPDS | FBS | 582 |

[1] nmoles of o-nitrophenol formed per min. per mg of protein
[2] control

The results indicate that the increase in transfection efficiency is due to the LPDS in the transfection medium. The serum used in the growth medium has no effect on transfection efficiency. Addition of LPDS to the transfection medium results in higher transfection efficiencies than FBS when the "standard CaPO$_4$ transfection method" is used.

EXAMPLE 37

Comparison of Different Hydroxylated Sterols (FBS Control).

The method of Example 2 was repeated. The results are shown in Table IX.

EXAMPLE 38

Comparison of Different Hydroxylated Sterols (HS Control)

The method of Example 7 was repeated. The results are shown in Table IX.

EXAMPLE 39

Comparison of Different Hydroxylated Sterols

The method of Example 7 was repeated, except 2.5 µg/ml of 25-hydroxycholesterol was added to the transfection reaction. The results are shown in Table IX.

EXAMPLE 40

Comparison of Different Hydroxylated Sterols

The method of Example 7 was repeated, except 2.5 µg/ml of 5-cholestan-3$\beta$-ol-7-one, supplied by Steraloids Inc. of Wilton, N.H., was added to the transfection reaction. The results are shown in Table IX.

EXAMPLE 41

Comparison of Different Hydroxylated Sterols

The method of Example 7 was repeated, except 2.5 µg/ml of cholestan-3$\beta$, 5$\alpha$, 6$\beta$-triol, supplied by Steraloids Inc. of Wilton, N.H., was added to the transfection reaction. The results are shown in Table IX.

EXAMPLE 42

Comparison of Different Hydroxylated Sterols

The method of Example 7 was repeated, except 2.5 µg/ml of 5$\beta$-cholanic acid-3$\alpha$, 7$\alpha$, 12-triol, supplied by Seraloids Inc. of Wilton, N.H., was added to the transfection reaction. The results are shown in Table IX.

EXAMPLE 43

Comparison of Different Hydroxylated Sterols

The method of Example 7 was repeated, except 2.5 μg/ml of 5β-cholanic acid-3,7,12-trione, supplied by Steraloids Inc. of Wilton, N.H., was added to the transfection reaction. The results are shown in Table IX.

TABLE IX

| Ex. | Serum | Hydroxysterol | β-gal Activity[1] | Rel. Transfec. Efficiency[2] |
|---|---|---|---|---|
| 37[3] | FBS | none | 0.3 | 1 |
| 38 | HS | none | 23.4 | 78 |
| 39 | HS | 25-HC[4] | 55.9 | 186 |
| 40 | HS | C-7-one[5] | 25.6 | 85 |
| 41 | HS | C-triol[6] | 15.8 | 53 |
| 42 | HS | CA-triol[7] | 29.5 | 98 |
| 43 | HS | CA-trione[8] | 16.9 | 56 |

[1] nmoles of o-nitrophenol formed per min. per mg of protein
[2] relative transfection efficiency is calculated by dividing the units of β-gal activity in the test sample by the units of β-gal activity in the control (the transfection performed with medium supplemented with 10% by volume FBS).
[3] control
[4] 25-hydroxycholesterol
[5] 5-cholestan-3β-ol-7-one
[6] cholestan-3β,6α,6β-triol
[7] 5β-cholanic acid-3α,7α,12-triol
[8] 5β-cholanic acid-3,7,12-trione The results indicate that significant enhancement of the transfection efficiency is obtained with 25-hydroxycholesterol.

EXAMPLE 44

Effect of Sera from Different Animals on Transfection Efficiency

The procedure described in Example 2 was repeated. The results are shown in Table X.

EXAMPLE 45

Effect of Sera from Different Animals on Transfection Efficiency

The procedure described in Example 19 was repeated. The results are shown in Table X.

EXAMPLE 46

Effect of Calf Serum on Transfection Efficiency

The procedure described in Example 19 was repeated, except 10% calf serum (supplied by GIBCO) was used in place of the human serum. The results are shown in Table X.

EXAMPLE 47

Effect of Newborn Calf Serum on Transfection Efficiency

The procedure described in Example 19 was repeated, except 10% newborn calf serum (supplied by GIBCO) was used in place of the human serum. The results are shown in Table X.

EXAMPLE 48

Effect of Lamb Serum on Transfection Efficiency

The procedure described in Example 19 was repeated, except 10% lamb serum (supplied by GIBCO) was used in place of the human serum. The results are shown in Table X.

EXAMPLE 49

Effect of Horse Serum on Transfection Efficiency

The procedure described in Example 19 was repeated, except 10% horse serum (supplied by GIBCO) was used in place of the human serum. The results are shown in Table X.

EXAMPLE 50

Effect of Chicken Serum on Transfection Efficiency

The procedure described in Example 19 was repeated, except 10% chicken serum (supplied by GIBCO) was used in place of the human serum. The results are shown in Table X.

EXAMPLE 51

Effect of Pig Serum on Transfection Efficiency

The procedure described in Example 19 was repeated, except 10% pig serum (supplied by GIBCO) was used in place of the human serum. The results are shown in Table X.

TABLE X

| Ex. | Serum | β-gal Activity[1] | Rel. Transfec. Efficiency[2] |
|---|---|---|---|
| 44[3] | Fetal bovine | 0.3 | 1 |
| 45 | Human[4] | 103 | 343 |
| 46 | Calf[4] | 155 | 517 |
| 47 | Newborn calf[4] | 49 | 165 |
| 48 | Lamb[4] | 89 | 297 |
| 49 | Horse[4] | 115 | 382 |
| 50 | Chicken[4] | 10 | 34 |
| 51 | Pig[4] | 89 | 269 |

[1] nmoles of o-nitrophenol formed per min. per mg of protein
[2] relative transfection efficiency is calculated by dividing the units of β-gal activity in the test sample by the units of β-gal activity in the control (the transfection performed with medium supplemented with 10% by volume FBS).
[3] control
[4] 2.5 μg/ml 25-hydroxycholesterol was included in the transfection experiment The results indicate that significant enhancement over the control transfection efficiency is obtained with human, calf, lamb, horse and pig sera. Higher transfection efficiencies where obtained with newborn calf and chicken sera than were obtained with FBS.

The above descriptions of exemplary embodiments of methods for improved mammalian cell transfection are for illustrative purposes. Because of variations which will be apparent to those skilled in the art, the present invention is not intended to be limited to the particular embodiments described above. The present invention may also be practiced in the absence of any element not specifically disclosed. The scope of the invention is defined by the following claims.

What is claimed is:

1. A process for transfecting a mammalian cell with exogenous DNA comprising:
   growing a mammalian cell in a growth medium comprising fetal bovine serum;
   replacing the growth medium comprising fetal bovine serum with a transfection medium comprising a second serum supplemented with 25-hydroxycholestrol, where the second serum is not fetal bovine serum;
   adding a calcium phosphate-DNA precipitate solution to the transfection medium over the cell to form a calcium phosphate-DNA precipitate/medium mixture;
   washing the cell; and incubating the cell in the presence of a growth medium.

2. A process as recited in claim 1 wherein the fetal bovine serum is present at a concentration of 5% to 20%, by volume, of the growth medium.

3. A process as recited in claim 1 wherein the second serum is present at a concentration of 5% to 20%, by volume of the transfection medium.

4. A process as recited in claim 1 wherein the 25-hydroxycholesterol is present at a concentration of 0.1 $\mu$g/ml to 5 $\mu$g/ml.

5. A process as recited in claim 1 wherein the 25-hydrocholesterol sterol is present at a concentration of 1 $\mu$g/ml to 5 $\mu$g/ml.

6. A process as recited in claim 1 wherein the 25-hydroxycholesterol is present at a concentration of 2.5 $\mu$g/ml.

7. A process as recited in claim 1 wherein the calcium phosphate-DNA precipitate solution comprises:
   125 mM calcium chloride;
   25 mM N,N-bis(2-hydroxyethyl)-2-aminoethane-sulfonic acid, pH 6.9 to 7.0;
   140 mM sodium chloride; and
   0.75 mM sodium phosphate.

8. A process as recited in claim 1 wherein the cell is incubated in the presence of the calcium phosphate-DNA precipitate/medium mixture for 1 to 6 hours.

9. A process as recited in claim 1 wherein the cell is incubated in the presence of the calcium phosphate-DNA precipitate/medium mixture for 3 to 4 hours.

10. A process for transfecting a mammalian cell with exogenous DNA comprising:
   growing a mammalian cell culture in a medium supplemented with fetal bovine serum;
   removing the medium and supplement from the cell;
   adding a transfection medium supplemented with 10%, by volume, of a serum and 2.5 $\mu$g/ml 25-hydroxycholesterol to a mammalian cell culture, wherein the serum is selected from the group consisting of human, newborn calf, calf, horse, lamb, and pig sera;
   adding a calcium phosphate-DNA precipitate solution to the transfection medium over the cell to form a calcium phosphate-DNA precipitate/medium mixture;
   incubating the cell in the presence of the calcium phosphate-DNA precipitate/medium mixture at 35° C. to 37° C. in an atmosphere of 3% to 5%, by volume, carbon dioxide for less than 6 hours;
   washing the cell; and
   incubating the cell in the presence of medium supplemented with fetal bovine serum at 37° C. in an atmosphere of 5%, by volume, carbon dioxide.

* * * * *

UNITED STATES PATENT AND TRADEMARK OFFICE
CERTIFICATE OF CORRECTION

PATENT NO. : 5,330,904
DATED : July 19, 1994
INVENTOR(S) : David H. Spear; Peter A. Edwards It is certified that error appears in the above-indentified patent and that said Letters Patent is hereby corrected as shown below:

Column 4, line 21, before "streptomycin" insert -- as --.
Column 4, line 68, change "hyroxyethyl" to
    -- hydroxyethyl --.
Column 8, line 35, change "βgal" to -- β-gal --.
Column 8, line 64, change "precipate" to
    -- precipitate --.
Column 9, line 11, before "900" change "of" to -- to --.
Column 16, line 67, change "Seraloids" to
    -- Steraloids --.
Column 17, line 25, change "6α" to -- 5α --.
Column 18, line 43, change "where" to -- were --.

Column 19, line 13, change "hydrocholesterol" to
    -- hydroxycholesterol --.

Signed and Sealed this

Seventh Day of February, 1995

Attest:

BRUCE LEHMAN

*Attesting Officer*            *Commissioner of Patents and Trademarks*